(12) United States Patent
Kobayashi et al.

(10) Patent No.: US 7,659,424 B2
(45) Date of Patent: Feb. 9, 2010

(54) PROCESS FOR THE ALLYLATION OF N-ACYLHYDRAZONES

(75) Inventors: Shu Kobayashi, Tokyo (JP); Masaharu Sugiura, Kanagawa (JP)

(73) Assignee: Japan Science and Technology Agency, Saitama (JP)

( * ) Notice: Subject to any disclaimer, the term of this patent is extended or adjusted under 35 U.S.C. 154(b) by 554 days.

(21) Appl. No.: 10/591,094

(22) PCT Filed: Feb. 24, 2005

(86) PCT No.: PCT/JP2005/002981

§ 371 (c)(1),
(2), (4) Date: Aug. 29, 2006

(87) PCT Pub. No.: WO2005/082840

PCT Pub. Date: Sep. 9, 2005

(65) Prior Publication Data

US 2007/0142672 A1    Jun. 21, 2007

(30) Foreign Application Priority Data

Mar. 1, 2004 (JP) .............................. 2004-056877
Aug. 25, 2004 (JP) .............................. 2004-244685

(51) Int. Cl.
C07C 241/02 (2006.01)
C07C 227/04 (2006.01)
C07C 229/08 (2006.01)
C07C 243/38 (2006.01)

(52) U.S. Cl. .......................... 560/34; 562/524; 562/575
(58) Field of Classification Search .................. 560/34; 562/524, 575

See application file for complete search history.

(56) References Cited

FOREIGN PATENT DOCUMENTS

CA    2 456 172 A1    4/2003
GB    1 493 237 A    11/1977

OTHER PUBLICATIONS

Ogawa et al., The Chemical Society of Japan Koen Yokoshu, 84(2):1270 (2004).
Ferraris et al., "Catalytic, Enantioselective Alkylations of N,O-Acetals", J. Org. Chem., 64:2168-2169 (1999).
Hamada et al., "Catalytic Asymmetric Allylation of Hydrazono Esters in Aqueous Media by Using $ZnF_2$-Chiral Diamine", Angew. Chem. Int. Ed., 42:3927-3930 (2003).
Chikako Ogawa et al., "Stereospecific, Enantioselective Allylation of α-Hydrazono Esters by Using Allyltrichlorosilanes with BINAP Dioxides as Neutral-Coordinate Organocatalysts", Angewandte Chemie, International Edition, 43(47), pp. 6491-6493 (2004).
Chikako Ogawa et al., "Phosphine Oxides as Efficient Neutral Coordinate-Organocatalysts for Stereoselective Allylation of N-acylhydrazones", Organic & Biomolecular Chemistry, 2(4), pp. 446-448 (2004).
Database WPI Week 200382, Derwent Publication Ltd., London, GB; XP-002464497; AN 2003-884288 (Sep. 25, 2003).

*Primary Examiner*—Peter G O'Sullivan
(74) *Attorney, Agent, or Firm*—Peter F. Corless; Christine C. O'Day; Edwards Angel Palmer & Dodge LLP

(57) ABSTRACT

[PROBLEMS] To provide a novel method for the allylation of N-acylhydrazones by which enantioselectively allylated N-acylhydrazines can be efficiently obtained.

[MEANS FOR SOLVING PROBLEMS] A method for the production of enantioselectively allylated N-acylhydrazines represented by the general formula [3]:

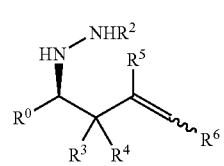

[3]

[wherein $R^0$ is an optionally substituted hydrocarbon group, an optionally substituted heterocyclic group, or —$COOR^1$ (wherein $R^1$ is a hydrocarbon group); $R^2$ is acyl; $R^3$ and $R^4$ are each hydrogen, or one of $R^3$ and $R^4$ is hydrogen and the other is a hydrocarbon group; and $R^5$ and $R^6$ are each independently hydrogen or a hydrocarbon group], characterized by reacting an N-acylhydrazone represented by the general formula [1]:

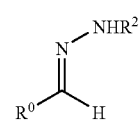

[1]

[wherein $R^0$ and $R^2$ are as defined above] with an allylating agent such as allyltrichlorosilane or crotyltrichlorosilane in the presence of a chiral phosphine oxide.

12 Claims, No Drawings

US 7,659,424 B2

PROCESS FOR THE ALLYLATION OF N-ACYLHYDRAZONES

TECHNICAL FIELD

The present invention relates to a method for producing enantioselectively allylated N-acylhydrazine, by which an objective substance can be obtained with high stereoselectivity. Compounds obtained by this method can be transformed into α-amino acid derivatives by cleavage of N—N bond, followed by substitution with various functional groups.

BACKGROUND ART

Allylation of α-imino esters is one of useful synthesis reactions to provide various α-amino acid derivatives because products obtained by allylation of α-imino esters can be substituted with various functional groups. However, there are only a few cases of success of enantioselective allylation.

Lectka et al. and Jørgensen et al. have both reported that a catalyst prepared from a combination of BINAP and a copper salt effectively functions in enantioselective allylation of α-imino ester whose nitrogen is protected by a p-toluenesulfonyl group, with the use of allylsilane and allyltin as allylating agents (yield 85%, 90% ee and yield 91%, 83% ee, respectively)

(Non-patent document 1, Non-patent document 2).

Meanwhile, in general, N-acylhydrazones are valuable compounds as imine equivalents easy to handle in organic synthesis. The present inventors have previously shown that for the purpose of developing organic synthesis reaction using water as reaction medium, a zinc fluoride-chiral diamine complex effectively promotes allylation reaction in which α-hydrazono ester is used instead of α-imino ester easily hydrolyzed in the presence of water, and have for the first time achieved enantioselective allylation of imine in a water-based solvent (yield 85%, 90% ee) (Non-patent document 3). In addition, the present inventors have found and reported that a complex obtained from a copper salt and chiral diamine effectively functions in allylation of α-imino ester (Non-patent document 4).

Non-patent document 1: T. Lectka et al., J. Org. Chem., 1999, vol. 64, pp. 2168-2169
Non-patent document 2: K. A. Jørgensen et al., J. Org. Chem., 1999, vol. 64, pp. 4844-4849
Non-patent document 3: T. Hamada et al., Angew. Chem. Int. Ed., 2003, vol. 42, pp. 3927-3930
Non-patent document 4: Y. Nakamura et al., Org. Lett., 2003, vol. 5, 2481, unpublished results

DISCLOSURE OF THE INVENTION

Problem to be Solved by the Invention

It is an object of the present invention to provide a novel method for allylation of N-acylhydrazone, by which enantioselectively allylated N-acylhydrazine can be efficiently obtained.

Means for Solving the Problem

The present invention is directed to a method for producing enantioselectively allylated N-acylhydrazine represented by the following general formula (3):

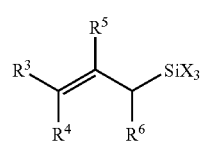

[3]

wherein $R^0$ represents an optionally substituted hydrocarbon group, an optionally substituted heterocyclic group, or —$COOR^1$ (where $R^1$ represents a hydrocarbon group); $R^2$ represents an acyl group; $R^3$ and $R^4$ each represent a hydrogen atom, or one of $R^3$ and $R^4$ represents a hydrogen atom and the other represents a hydrocarbon group; $R^5$ and $R^6$ each independently represent a hydrogen atom or a hydrocarbon group; and $R^4$ and $R^6$ may together form an alkylene ring or a heterocycle, the method characterized by reacting, in the presence of chiral phosphine oxide, N-acylhydrazone represented by the following general formula (1):

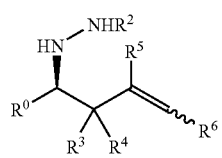

[1]

wherein $R^0$ and $R^2$ are as defined above, with an allylating reagent represented by the following general formula (2):

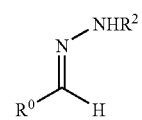

[2]

wherein $R^3$, $R^4$, $R^5$, and $R^6$ are as defined above; $R^4$ and $R^6$ may together form an alkylene ring or a heterocycle; and three Xs each represent a chlorine atom or a bromine atom, or two of the three Xs each represent a chlorine atom or a bromine atom and the other one represents an alkyl group.

As a hydrocarbon group of the optionally substituted hydrocarbon group represented by $R^0$ in the general formulas (1) and (3), a hydrocarbon group represented by $R^1$ in —$COOR^1$ represented by $R^0$ in the general formulas (1) and (3), and hydrocarbon groups represented by $R^3$, $R^4$, $R^5$, and $R^6$ in the general formulas (2) and (3), saturated or unsaturated aliphatic hydrocarbon groups and aromatic hydrocarbon groups can be mentioned. Specific examples of such hydrocarbon groups include alkyl, cycloalkyl, alkenyl, cycloalkenyl, alkynyl, aralkyl, and aryl groups.

As the above alkyl groups, for example, linear or branched alkyl groups each having 1 to 20 carbon atoms, preferably 1 to 10 carbon atoms, more preferably 1 to 6 carbon atoms can be mentioned. Specific examples of such alkyl groups include methyl, ethyl, propyl, isopropyl, butyl, isobutyl, secondary butyl, tertiary butyl, pentyl, and hexyl groups.

As the above cycloalkyl groups, for example, monocyclic, polycyclic, or condensed cyclic cycloalkyl groups each having 3 to 30 carbon atoms, preferably 3 to 20 carbon atoms, more preferably 3 to 10 carbon atoms can be mentioned. Specific examples of such cycloalkyl groups include cyclopropyl, cyclopentyl, cyclohexyl, and cyclooctyl groups.

As the above alkenyl groups, for example, the above-mentioned alkyl groups each having two or more carbon atoms and one or more double bonds can be mentioned. Specific examples of such alkenyl groups include vinyl, allyl, 1-propenyl, isopropenyl, 2-butenyl, 1,3-butadienyl, 2-pentenyl, and 2-hexenyl groups.

As the above cycloalkenyl groups, for example, the above-mentioned cycloalkyl groups each having one or more double bonds can be mentioned. Specific examples of such cycloalkenyl groups include cyclopentenyl and cyclohexenyl groups.

As the above alkynyl groups, for example, the above-mentioned alkyl groups each having two or more carbon atoms and one or more triple bonds can be mentioned. Specific examples of such alkynyl groups include ethynyl, 1-propynyl, and 2-propynyl groups.

As the above aralkyl groups, for example, monocyclic, polycyclic, or condensed cyclic aralkyl groups each having 7 to 30 carbon atoms, preferably 7 to 20 carbon atoms, more preferably 7 to 15 carbon atoms can be mentioned. Specific examples of such aralkyl groups include benzyl, phenethyl, naphthylmethyl, and naphthylethyl groups.

As the above aryl groups, for example, monocyclic, polycyclic, or condensed cyclic aromatic hydrocarbon groups each having 6 to 30 carbon atoms, preferably 6 to 20 carbon atoms, more preferably 6 to 14 carbon atoms can be mentioned. Specific examples of such aryl groups include phenyl, tolyl, xylyl, naphthyl, methylnaphthyl, anthryl, phenanthryl, and biphenyl groups.

As a heterocyclic group of the optionally substituted heterocyclic group represented by $R^0$ in the general formulas (1) and (3), a saturated or unsaturated monocyclic, polycyclic, or condensed cyclic heterocyclic group which contains at least one heterocyclic nitrogen, oxygen and/or sulfur atom, and each ring of which is a 5- to 20-membered ring, preferably a 5- to 10-membered ring, more preferably a 5- to 7-membered ring, and which may be condensed with a carbocyclic group such as a cycloalkyl, cycloalkenyl, or aryl group can be mentioned. Specific examples of such a heterocyclic group include pyridyl, thienyl, phenylthienyl, thiazolyl, furyl, piperidyl, piperazyl, pyrrolyl, morpholino, imidazolyl, indolyl, quinolyl, and pyrimidinyl groups.

A substituent of the optionally substituted hydrocarbon group or heterocyclic group represented by $R^0$ in the general formulas (1) and (3) is not particularly limited as long as it does not interfere with asymmetric allylation reaction according to the present invention. Examples of such a substituent include alkyl, cycloalkyl, alkenyl, cycloalkenyl, alkynyl, aralkyl, aryl, alkoxy, ester, nitro, ether, amide, cyano, and silyl groups and a halogen atom.

Examples of the acyl group represented by R in the general formulas (1) and (3) include benzoyl, acetyl, propionyl, and butyryl groups. Among these groups, a benzoyl group is preferably used.

In a case where $R^4$ and $R^6$ together form an alkylene ring in the general formulas (2) and (3), examples of such an alkylene ring include cyclopentene, cyclohexene, cycloheptene, cyclooctene, cyclohexadiene, cycloheptadiene, and cyclooctadiene.

On the other hand, in a case where $R^4$ and $R^6$ together form a heterocycle in the general formulas (2) and (3), examples of such a heterocycle include the same heterocycles as mentioned above with reference to a heterocycle of the optionally substituted heterocyclic group represented by $R^0$.

As described above, in the general formula (2), three Xs each represent a chlorine atom or a bromine atom, or two of the three Xs each represent a chlorine atom or a bromine atom and the other one represents an alkyl group. In the latter case, examples of the alkyl group include linear or branched alkyl groups each having 1 to 20 carbon atoms, preferably 1 to 10 carbon atoms, more preferably 1 to 6 carbon atoms. Specific examples of such an alkyl group include methyl, ethyl, propyl, isopropyl, butyl, isobutyl, secondary butyl, tertiary butyl, pentyl, and hexyl groups.

Specific examples of the allylating reagent represented by the general formula (2) to be used in the present invention include allyltrichlorosilane, crotyltrichlorosilane, methallyltrichlorosilane, and prenyltrichlorosilane.

Example of chiral phosphine oxide to be used in the present invention includes (R)- or (S)-2,2'-bis(diarylphosphino)-1,1'-binaphthyl dioxides (hereinafter, abbreviated as BINAP dioxides) represented by the following general formula (4):

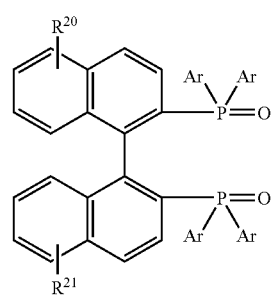

[4]

wherein $R^{20}$ and $R^{21}$ are each a substituent group on a naphthalene ring, and each independently represent a hydrogen atom, an alkyl group, an alkoxy group, or a halogen atom; and Ar represents an aryl group. In the general formula (4), the number of each of the substituent groups $R^{20}$ and $R^{21}$ on a naphthalene ring may be one, but may alternatively be two or more.

Preferred examples of the BINAP dioxide represented by the general formula (4) include BINAP dioxides in which $R^{20}$ and $R^{21}$ each represent a hydrogen atom, BINAP dioxides in which Ar represents a phenyl group, and BINAP dioxides in which Ar represents a tolyl group.

Specific examples of BINAP dioxides represented by the general formula (4) include (S)- or (R)-BINAP dioxides in which $R^{20}$ and $R^{21}$ each represent a hydrogen atom and Ar represents a phenyl group; and (S)- or (R)-Tol-BINAP dioxides in which $R^{20}$ and $R^{21}$ each represent a hydrogen atom and Ar represents a tolyl group. It is to be noted that "Tol" is an abbreviation for a tolyl group.

The amount of the BINAP dioxide to be used in the present invention is usually 1 or more equivalents, preferably 1.5 or more equivalents, more preferably 2 or more equivalents, with respect to the amount of N-acylhydrazone used.

The amount of the allylating reagent to be used in the present invention is usually 1 or more equivalents, preferably 1.2 or more equivalents, more preferably 1.5 or more equivalents, with respect to the amount of N-acylhydrazone used.

The reaction according to the production method of the present invention is usually carried out in an organic solvent. Preferred examples of an organic solvent to be used for the reaction include halogenated alkyls and the like. Among them, methylene chloride is particularly preferred.

The temperature for the reaction is usually −50° C. or less, preferably −60° C. or less, more preferably −70° C. or less, even more preferably in the neighborhood of −78° C.

The time for the reaction varies depending on the reaction temperature, the kind and amount of the allylating reagent or the chiral phosphine oxide to be used for the reaction, and other reaction conditions, but is usually in the range of several to a dozen or so hours.

Next, a brief description of the production method of the present invention will be given.

First, N-acylhydrazone as a reaction substrate and chiral phosphine oxide are dissolved or suspended in a solvent to obtain a solution or suspension, and then the solution or suspension is cooled to a predetermined temperature. Then, an allylating reagent is added to the solution or suspension being stirred, and a reaction mixture is continued to be stirred at a predetermined temperature to allow reaction to occur. The reaction is terminated by adding a reaction terminator such as an amine compound or the like. After the completion of the reaction, a reaction product is isolated and purified by post-treatment generally carried out in this field, such as extraction with an organic solvent, washing, dewatering and drying, concentration, distillation, purification using various chromatography techniques, and drying.

As described above, the production method of the present invention uses chiral phosphine oxide. In this regard, it is to be noted that various additives may be used together with chiral phosphine oxide for the purpose of reducing the amount of chiral phosphine oxide to be used.

Specific examples of such additives include phosphines that can be coordinated to a silicon atom of an allylating reagent used (e.g., allyltrichlorosilane, crotyltrichlorosilane), such as trialkylphosphines (e.g., tri-n-butylphosphine), triarylphosphines (e.g., triphenylphosphine), and alkyldiarylphosphines (e.g., diphenylmethylphosphine).

(2R, 3S)-ethyl 2-(N'-benzoylhydrazino)-3-methyl-4-pentenoate represented by the following formula (5):

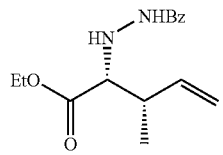

wherein Et represents an ethyl group and Bz represents a benzoyl group, which is obtained by the production method of the present invention can be transformed into a precursor of D-alloisoleusine relatively hard to obtain.

A simplified reaction scheme of a method for synthesizing D-alloisoleusine using the above-described precursor is shown below.

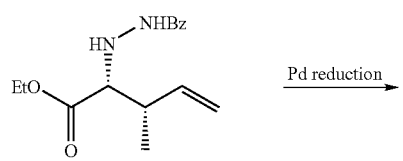

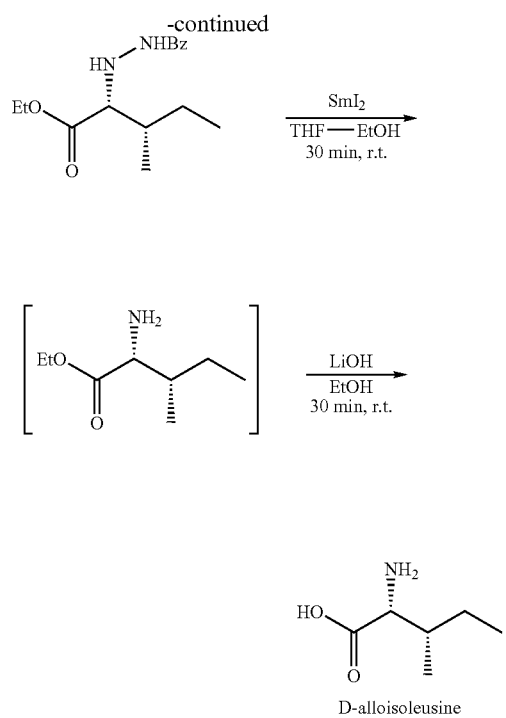

D-alloisoleusine

The reduction reaction shown in the scheme can be carried out by various hydrogenation reactions. Among them, catalytic hydrogenation using a noble metal catalyst such as palladium and hydrogen gas is preferably employed.

The reduction reaction is usually carried out at a room temperature in a reaction solvent such as ethanol. The time for the reduction reaction is usually about 10 to 20 hours. The yield is usually about 65 to 85%.

Next, cleavage of N—N bond is carried out. This reaction is preferably carried out in the usual manner using samarium iodide. After the completion of the cleavage reaction, subsequent hydrolysis is preferably carried out without isolating an intermediate because the intermediate does not absorb UV and therefore there is a fear that the intermediate is lost if it is isolated.

The reaction using samarium iodide is usually carried out at a room temperature in a THF-EtOH mixed solvent. The time for the reaction is usually about several tens of minutes.

The hydrolysis reaction is usually carried out at a room temperature using a strong alkali such as lithium hydroxide, and is achieved by stirring for about several tens of minutes. The total yield of two steps is usually about 70%.

As described above, it can be said that the enantioselective allylation reaction of N-acylhydrazone using chiral phosphine oxide according to the present invention provides an efficient method for the synthesis of α-amino acid derivatives.

Effect of the Invention

According to the present invention, it is possible to provide a method for producing enantioselectively allylated N-acylhydrazine efficiently. Further, allylated N-acylhydrazines produced by this method include one that can be transformed into a precursor of D-alloisoleusine relatively hard to obtain, from which D-alloisoleusine can be relatively easily obtained in good yield. Therefore, according to the present invention, it is also possible to provide a practical method for the synthesis of α-amino acid derivatives.

BEST MODE FOR CARRYING OUT THE INVENTION

Hereinbelow, the present invention will be more specifically described with reference to the following Examples, but the present invention is not limited thereto.

EXAMPLE 1

Synthesis of (R)-ethyl 2-(N'-benzoylhydrazino)-4-pentenoate

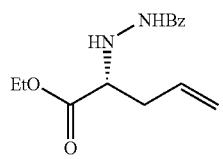

A methylene chloride solution (1.5 mL) of ethyl N-benzoylhydrazono acetate (22.0 mg, 0.1 mmol) and (S)-BINAP dioxide (130.9 mg, 0.2 mmol) was cooled to −78° C., and then a methylene chloride solution (0.5 mL) of allyltrichlorosilane (22 μL, 0.15 mmol) was added thereto. After the reaction mixture was stirred at −78° C. for 12 hours, a dehydrated ethanol solution (0.3 mL) of triethylamine (60 μL, 0.5 mmol) was added thereto to terminate reaction. The reaction mixture was heated to a room temperature, and was then subjected to extraction with methylene chloride three times. The thus obtained organic phase was washed with a saturated aqueous sodium chloride solution, and was then dried with sodium sulfate. The solvent was removed by distillation under a reduced pressure, and the residue was isolated and purified by silica gel thin layer chromatography (hexane/ethyl acetate=2/1) to obtain (R)-ethyl 2-(N'-benzoylhydrazino)-4-pentenoate (23.6 mg, yield: 91%, 98% ee).

EXAMPLE 2

Synthesis of (2R, 3R)-ethyl 2-(N'-benzoylhydrazino)-3-methyl-4-pentenoate

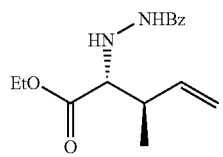

Reaction and post-treatment were carried out in the same manner as in the Example 1 except that allyltrichlorosilane was replaced with Z-crothyltrichlorosilane to obtain (2R, 3R)-ethyl 2-(N'-benzoylhydrazino)-3-methyl-4-pentenoate (yield: 96%, syn/anti=<1/>99, 96% ee):

$[\alpha]^{27}_D$+117.1(c0.13, CHCl$_3$, 95% ee); $^1$H NMR (300 MHz, CDCl$_3$) δ 1.10 (d, 3H, J=6.9 Hz), 1.22 (t, 3H, J=7.1 Hz), 2.60(sext, 1H, J=6.8 Hz), 3.59 (d, 1H, J=6.8 Hz), 3.88-3.95 (br, 1H), 4.09-4.29 (m, 2H), 5.07 (brd, 1H, J=10.5 Hz), 5.08 (brd, 1H, J=17.3 Hz), 5.78 (ddd, 1H, J=8.5, 10.5, 17.5 Hz), 7.33-7.57 (m, 3H), 7.64-7.83(m, 2H), 7.90 (brs, 1H); $^{13}$C NMR(75 MHz, CDCl$_3$) δ 14.3, 16.9, 39.8, 61.0, 67.9, 108.3, 116.7, 126.9, 128.7, 131.9, 138.9, 167.1, 172.4; IR (neat) 3288, 2981, 1733, 1705, 1404, 1200, 1029, 921, 694 cm$^{-1}$; HPLC (CHIRALPAK OD, 0.46 cmφ 25 cmL, hexane/2-propanol=9/1, flow rate: 1.0 mL/min, UV detection: 254 nm) $t_R$=9.1 min (2R, 3R), $t_R$=10.7 min (2S, 3S).

EXAMPLE 3

Synthesis of (2R, 3S)-ethyl 2-(N'-benzoylhydrazino)-3-methyl-4-pentenoate

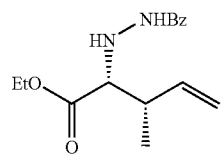

Reaction and post-treatment were carried out in the same manner as in the Example 1 except that allyltrichlorosilane was replaced with E-crothyltrichlorosilane to obtain (2R, 3S)-ethyl 2-(N'-benzoylhydrazino)-3-methyl-4-pentenoate (yield: 92%, syn/anti=98/2, >99% ee):

$[\alpha]^{27}_D$+36.0(c0.11,CHCl$_3$, 89%ee); $^1$H NMR (300 MHz, CDCl$_3$) δ 1.08 (d, 3H, J=6.9 Hz), 1.22 (t, 3H, J=7.1 Hz), 2.70-2.81 (m, 1H), 3.72 (brd, 1H, J=4.2 Hz), 4.08-4.26 (m, 2H), 5.14 (brd, 1H, J=10.5 Hz), 5.16 (brd, 1H, J=18.5 Hz), 5.34 (brs, 1H), 5.90 (ddd, 1H, J=6.5, 10.1, 17.1 Hz), 7.33-7.47 (m, 3H), 7.63-7.67 (m, 2H), 7.86 (brs, 1H); $^{13}$C NMR (75 MHz, CDCl$_3$) δ 14.2, 14.4, 38.7, 61.0, 66.7, 116.2, 126.9, 128.6, 131.9, 132.5, 138.9, 166.8, 172.3; IR (neat) 3292, 3068, 2979, 1733, 1557, 1201, 920, 696 cm$^{-1}$; Anal. Calcd for C$_{20}$H$_{13}$N$_2$O$_3$: C, 65.20; H, 7.30; N, 10.14. Found: C, 64.95; H, 7.24; N, 10.09; HPLC (CHIRALPAK OD, 0.46 cmφ 25 cmL, hexane/2-propanol=19/1, flow rate: 1.0 mL/min, UV detection: 254 nm) $t_R$=14.7 min (2R, 3S), $t_R$=16.5 min (2S, 3R).

EXAMPLE 4

Synthesis of (R)-ethyl 2-(N'-benzoylhydrazino)-4-methyl-4-pentenoate

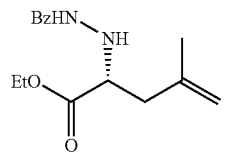

Reaction and post-treatment were carried out in the same manner as in the Example 1 except that allyltrichlorosilane was replaced with methallyltrichlorosilane and that the reaction time was changed to 6 hours to obtain (R)-ethyl 2-(N'-benzoylhydrazino)-4-methyl-4-pentenoate (yield: 83%, 94% ee):

$^1$H NMR (300 MHz, CDCl$_3$) δ 1.20 (d, 3H, J=7.3 Hz), 1.81 (s, 3H), 2.33 (dd, 1H, 9.7, 14.0 Hz), 2.98 (dd, 1H, J=4.1, 14.0 Hz), 3.88 (brs, 1H), 4.03-4.20 (m, 2H), 4.85 (brd, 2H, J=12.7

Hz), 7.33-7.46 (m, 3H), 7.66-7.69 (m, 2H), 8.14 (br, 2H); $^{13}$C NMR (75 MHz, CDCl$_3$) δ 14.1, 21.6, 39.4, 60.2, 61.1, 114.6, 126.9, 128.6, 131.9, 132.5, 140.6, 167.0, 173.0; IR (neat) 3297, 2924, 1726, 1639, 1466, 1384, 1027, 693, 610 cm$^{-1}$; HPLC (CHIRALPAK OD, 0.46 cmφ 25 cmL, hexane/2-propanol=9/1, flowrate: 1.0 mL/min, UV detection: 254 nm) t$_R$=8.7 min (R), t$_R$=11.4 min (S).

EXAMPLE 5

Synthesis of (R)-ethyl 2-(N'-benzoylhydrazino)-3,3'-dimethyl-4-pentenoate

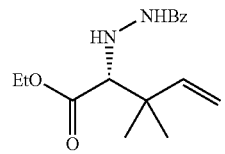

Reaction and post-treatment were carried out in the same manner as in the Example 1 except that allyltrichlorosilane was replaced with prenyltrichlorosilane to obtain (R)-ethyl 2-(N'-benzoylhydrazino)-3,3'-dimethyl-4-pentenoate (yield: 57%, 32% ee):

$^1$H NMR(400 MHz, CDCl$_3$) δ 1.09 (t, 3H), 1.11 (s, 3H), 1.21 (t, 3H, J=7.1 Hz), 2.56 (s, 1H), 4.17 (ddq, 1H, J=2.0, 3.7, 7.1), 5.08 (d, 1H, J=17.3 Hz), 5.10 (d, 1H, J=10.2 Hz), 5.93 (dd, 1H, J=10.3, 17.3 Hz), 7.33-7.63 (m, 7H); $^{13}$C NMR(100 MHz, CDCl$_3$)δ 14.3, 22.1, 25.3, 39.6, 60.8, 70.9, 113.7, 126.8, 128.6, 131.9, 132.5, 144.0, 167.2, 171.9; IR (neat) 3297, 2924, 1726, 1638, 1466, 1384, 1027, 693, 610 cm$^{-1}$; (CHIRALPAK OD, 0.46 cmφ 25 cmL, hexane/2-propanol=9/1, flowrate: 0.3 mL/min, UV detection: 254 nm) t$_R$=25.6 min (R), t$_R$=28.8 min (S)

EXAMPLE 6

Synthesis of (R)-isopropyl 2-(N'-benzoylhydrazino)-4-pentenoate

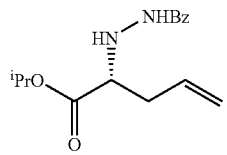

Reaction and post-treatment were carried out in the same manner as in the Example 1 except that ethyl N-benzoylhydrazono acetate was replaced with isopropyl N-benzoylhydrazono acetate to obtain (R)-isopropyl 2-(N'-benzoylhydrazino)-4-pentenoate (yield: 70%, 97% ee):

[α]$^{27}$$_D$+37.6 (c0.30, CHCl$_3$, 97%ee); $^1$H NMR (300 MHz, CDCl$_3$) δ 1.19 (d, 6H, J=5.7 Hz), 2.37-2.47 (m, 1H), 2.52-2.59 (m, 2H), 3.75 (dd, 1H, J=5.2, 7.2 Hz), 4.46 (brs, 1H), 4.98-5.23 (m, 2H), 5.74-5.88 (m, 1H), 7.34-7.48 (m, 3H), 7.66-7.69 (m, 2H), 8.07 (brs, 1H); $^{13}$C NMR (75 MHz, CDCl$_3$) δ 21.8, 35.1, 62.1, 68.9, 119.0, 126.9, 128.7, 131.9, 132.4, 132.7, 166.8, 172.0; IR (neat) 3302, 2981, 1730, 1643, 1464, 1105, 694 cm$^{-1}$.

EXAMPLE 7

Synthesis of (R)-cyclohexyl 2-(N'-benzoylhydrazino)-4-pentenoate

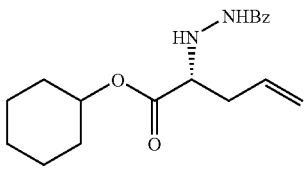

Reaction and post-treatment were carried out in the same manner as in the Example 1 except that ethyl N-benzoylhydrazono acetate was replaced with cyclohexyl N-benzoylhydrazono acetate to obtain (R)-cyclohexyl 2-(N'-benzoylhydrazino)-4-pentenoate (yield: 28%, 98% ee):

[α]$^{27}$$_D$+32.3 (c0.11, CHCl$_3$, 98% ee); $^1$H NMR (300 MHz, CDCl$_3$) δ 1.15-1.49 (m, 6H), 1.64-1.69 (m, 2H), 1.77-1.79 (m, 2H), 2.42-2.49 (m, 1H), 2.57-2.62 (m, 1H), 3.81 (brs, 1H), 4.76-4.83 (m, 1H), 5.12-5.23 (m, 2H), 5.76-5.86 (m, 1H), 7.34-7.39 (m, 2H), 7.42-7.48 (m, 1H), 7.67-7.70 (m, 2H), 8.18 (brs, 1H); $^{13}$C NMR (75 MHz, CDCl$_3$)δ 23.6, 25.2, 31.5, 35.0, 62.1, 73.9, 77.2, 119.2, 120.7, 132.1, 132.2, 132.5, 162.6, 166.7; IR (neat) 3293, 1734, 1651, 1541, 1070, 669 cm$^{-1}$.

EXAMPLE 8

Synthesis of (R)-benzyl 2-(N'-benzoylhydrazino)-4-pentenoate

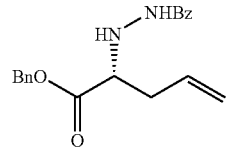

Reaction and post-treatment were carried out in the same manner as in the Example 1 except that ethyl N-benzoylhydrazono acetate was replaced with benzyl N-benzoylhydrazono acetate to obtain (R)-benzyl 2-(N'-benzoylhydrazino)-4-pentenoate (yield: 12%, 91% ee):

[α]$^{27}$$_D$−636.2 (cO.04, CHCl$_3$, 91% ee); $^1$H NMR (300 MHz, CDCl$_3$) δ 2.43-2.50 (m, 1H), 2.56-2.65 (m, 1H), 3.87-3.91 (m, 1H), 3.83-4.02 (br, 1H), 5.06-5.24 (m, 4H), 5.71-5.82 (m, 1H), 7.20-7.62 (m, 10H), 8.11 (brs, 1H); $^{13}$C NMR (75 MHz, CDCl$_3$) δ 34.8, 62.2, 67.9, 77.2, 119.4, 126.9, 127.0, 128.4, 128.5, 128.66, 128.69, 132.1, 132.3, 135.3, 166.8, 171.9; IR (neat) 3327, 2346, 1736, 1633, 1092, 916, 800, 752, 692 cm$^1$; Anal. Calcd for C$_{19}$H$_{20}$N$_2$O$_3$: C, 70.35; H, 6.21; N, 8.64. Found: C, 70.31; H, 6.27; N, 8.65.

EXAMPLE 9

Synthesis of (2S, 3R)-ethyl 2-(N'-benzoylhydrazino)-3,4-dimethyl-4-pentenoate

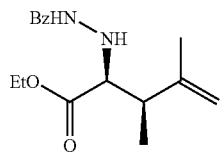

Reaction and post-treatment were carried out in the same manner as in the Example 1 except that allyltrichlorosilane was replaced with E-2-methyl-2-butenyltrichlorosilane and that (S)-BINAP dioxide was replaced with (R)-Tol-BINAP dioxide to obtain (2S, 3R)-ethyl 2-(N'-benzoylhydrazino)-3,4-dimethyl-4-pentenoate (yield: 80%, syn/anti=98/2, 96% ee):

$[\alpha]^{27}_D$–64.1 (c0.10, CHCl$_3$, 96%ee); $^1$H NMR (300 MHz, CDCl$_3$) δ 1.09 (d, 3H, J=7.0 Hz), 1.23 (t, 3H, J=7.0 Hz), 1.87 (s, 3H), 2.68 (qd, 1H, J=7.0 Hz), 3.26 (br, 1H), 3.87 (d, 1H, J=4.8 Hz), 4.08-4.26 (m, 2H), 4.87 (brs, 1H), 4.97 (brs, 1H), 7.33-7.54 (m, 3H), 7.63-7.66 (m, 2H), 7.89 (brs, 1H); $^{13}$C NMR (75 MHz, CDCl$_3$) δ 13.6, 14.2, 21.5, 41.6, 61.1, 64.1, 77.2, 113.0, 126.8, 128.7, 132.0, 145.5, 166.7, 172.5; IR (neat) 3296, 2976, 1734, 1647, 1460, 1198, 901, 712 cm$^{-1}$; Anal. Calcd for C$_{16}$H$_{22}$N$_2$O$_3$: C, 65.88; H, 7.63; N, 9.52. Found: C, 66.18; H, 7.64; N, 9.65; HPLC (CHIRALPAK OD, 0.46 cmφ 25 cmL, hexane/2-propanol=9/1, flowrate: 0.8 mL/min, UV detection: 254 nm) t$_R$=8.7 min (2S, 3R), t$_R$=10.0 min (2R, 3S).

EXAMPLE 10

Synthesis of (2S, 3S)-ethyl 2-(N'-benzoylhydrazino)-3,4-dimethyl-4-pentenoate

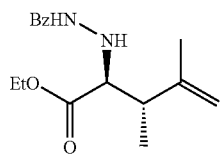

Reaction and post-treatment were carried out in the same manner as in the Example 1 except that allyltrichlorosilane was replaced with Z-2-methyl-2-butenyltrichlorosilane and that (S)-BINAP dioxide was replaced with (R)-Tol-BINAP dioxide to obtain (2S, 3S)-ethyl 2-(N'-benzoylhydrazino)-3,4-dimethyl-4-pentenoate (yield: 80%, syn/anti=<1/>99, 81% ee):

$[\alpha]^{27}_D$–74.8 (c0.15, CHCl$_3$, 72%ee); $^1$H NMR (300 MHz, CDCl$_3$) δ 1.04 (d, 3H, J=7.1 Hz), 1.22 (t, 3H, J=7.1 Hz), 1.80 (s, 3H), 2.62 (qd, 1H, J=7.1, 9.2 Hz), 3.77 (d, 1H, J=9.2 Hz), 4.27 (qd, 2H, J=1.1, 7.1 Hz), 4.90 (d, 1H, J=6.1 Hz), 4.91 (d, 1H, J=6.1 Hz), 7.34-7.48 (m, 4H), 7.64-7.68 (m, 2H), 8.06 (br, 1H); $^{13}$C NMR (75 MHz, CDCl$_3$) δ 14.3, 16.3, 18.3, 42.8, 61.1, 65.8, 77.2, 114.1, 127.0, 128.7, 132.1, 145.3, 167.4, 172.5; IR (neat) 3311, 1734, 1651, 1458, 1093, 903, 696 cm$^{-1}$; HPLC (CHIRALPAK OD, 0.46 cmφ 25 cmL, hexane/2-propanol=9/1, flowrate: 0.8 mL/min, UV detection: 254 nm) t$_R$=8.7 min (2R, 3R), t$_R$=10.4 min (2S, 3S).

EXAMPLE 11

Synthesis of (S)-ethyl 2-(N'-benzoylhydrazino)-4-phenyl-4-pentenoate

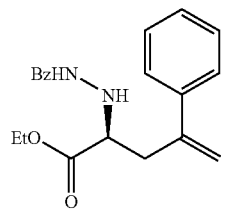

Reaction and post-treatment were carried out in the same manner as in the Example 1 except that allyltrichlorosilane was replaced with 2-phenyl-2-propenyltrichlorosilane and that (S)-BINAP dioxide was replaced with (R)-Tol-BINAP dioxide to obtain (S)-ethyl 2-(N'-benzoylhydrazino)-4-phenyl-4-pentenoate (yield: 50%, 95% ee):

$[\alpha]^{27}_D$–36.5 (c0.11, CHCl$_3$, 97%ee); $^1$H NMR (300 MHz, CDCl$_3$) δ 1.19 (t, 3H, J=7.1 Hz), 2.82 (dd, 1H, J=8.3, 14.3 Hz), 3.05 (dd, 1H, J=4.6, 14.3 Hz), 3.70-3.83 (m, 1H), 3.70-4.03 (br, 1H), 4.07 (q, 2H, J=7.1 Hz), 5.26 (brs, 1H), 5.38 (brs, 1H), 7.19-7.45 (m, 8H), 7.59-7.62 (m, 2H), 7.88 (brs, 1H); $^{13}$C NMR (75 MHz, CDCl$_3$) δ 14.1, 36.8, 61.3, 77.2, 116.3, 126.9, 127.9, 128.5, 128.6, 132.0, 132.3, 139.9, 143.7, 162.3, 166.6; IR (neat) 3342, 2927, 1655, 1460, 1093, 474 cm$^{-1}$; Anal. Calcd for C$_{20}$H$_{22}$N$_2$O$_3$: C, 70.50; H, 6.68; N, 8.27. Found: C, 70.99; H, 6.55; N, 8.28; HPLC(CHIRALPAK OD, 0.46 cmφ 25 cmL, hexane/2-propanol=9/1, flow rate: 2.0 mL/min, UV detection: 254 nm) t$_R$=5.9 min (R), t$_R$=17.1 min (S).

REFERENCE EXAMPLE 1

Reduction Reaction of Olefin Group

10% palladium activated carbon (20 mg) was added to an ethanol solution (5 mL) of (2R, 3S)-ethyl 2-(N'-benzoylhydrazino)-3-methyl-4-pentenoate (116 mg, 0.4 mmol), and the reaction mixture was stirred at a room temperature for 12 hours. The reaction mixture was filtered to obtain filtrate, and the palladium activated carbon was washed with ethanol (15 mL). The filtrate and the ethanol were distillated under a reduced pressure to remove the solvent, and the residue was purified and isolated by silica gel column chromatography (hexane/ethyl acetate=2/1) to obtain (2R, 3S)-ethyl 2-(N'-benzoylhydrazino)-3-methylpentanoate (80 mg, yield: 70%):

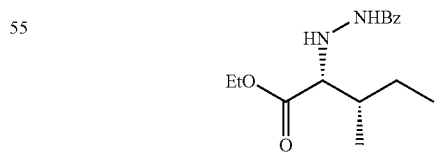

$^1$H NMR (400 MHz, CDCl$_3$) δ 0.92 (d, 3H, J=7.1 Hz), 0.94 (t, 3H, J=7.3 Hz), 1.17-1.33 (m, 1H), 1.21 (t, 3H, J=7.3 Hz), 1.52-1.62 (m, 1H), 1.83-1.92 (m, 1H), 3.63 (d, 1H, J=4.15 Hz), 4.07-4.22 (m, 2H), 4.22-5.00 (brs, 1H), 7.32-7.36 (m, 2H), 7.41-7.45 (m, 1H), 7.65-7.70 (m, 2H), 8.02 (brs, 1H); $^{13}$C NMR (75 MHz, CDCl$_3$) δ 11.8, 14.2, 14.9, 26.2, 36.7, 60.9, 67.0, 126.8, 128.6, 131.8, 132.6, 166.8, 173.2; IR (neat) 3311, 2968, 1732, 1651, 1604, 1579, 1403, 1201, 1094, 845, 694 cm$^{-1}$.

INDUSTRIAL APPLICABILITY

As described above, enantioselectively allylated N-acylhydrazines efficiently produced by the method according to the present invention include one that can be transformed into a precursor of D-alloisoleusine relatively hard to obtain, from which D-alloisoleusine can be relatively easily obtained in good yield. Since conventional methods for synthesizing alloisoleusine leave room for improvement in practical use, the present invention has great value in that it can provide a practical method for the synthesis of α-amino acid derivatives.

What is claimed is:

1. A method for producing enantioselectively allylated N-acylhydrazine represented by the following general formula (3):

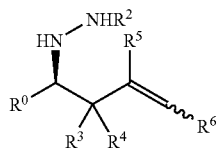

[3]

wherein $R^0$ represents an optionally substituted hydrocarbon group, an optionally substituted heterocyclic group or —COOR$^1$ (where R$^1$ represents a hydrocarbon group); R$^2$ represents an acyl group; R$^3$ and R$^4$ each represent a hydrogen atom, or one of R$^3$ and R$^4$ represents a hydrogen atom and the other represents a hydrocarbon group; R$^5$ and R$^6$ each independently represent a hydrogen atom or a hydrocarbon group; and R$^4$ and R$^6$ may together form an alkylene ring or a heterocycle, the method characterized by reacting, in the presence of chiral phosphine oxide, N-acylhydrazone represented by the following general formula (1):

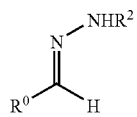

[1]

wherein R$^0$ and R$^2$ are as defined above,
with an allylating reagent represented by the following general formula (2):

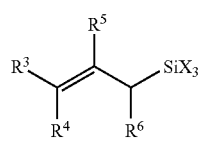

[2]

wherein R$^3$, R$^4$, R$^5$, and R$^6$ are as defined above; R$^4$ and R$^6$ may together form an alkylene ring or a heterocycle; and three Xs each represent a chlorine atom or a bromine atom, or two of the three Xs each represent a chlorine atom or a bromine atom and the other one represents an alkyl group.

2. The method according to claim 1, wherein R$^0$ in the general formulas (1) and (3) is —COOR$^1$ (where R$^1$ represents a hydrocarbon group).

3. The method according to claim 1, wherein the chiral phosphine oxide is (R)- or (S)-2,2'-bis(diarylphosphino)-1,1'-binaphthyl dioxide represented by the following general formula (4):

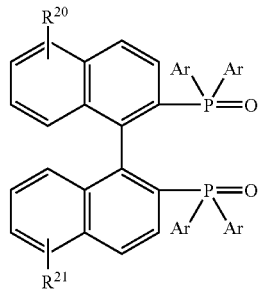

[4]

wherein $R^{20}$ and $R^{21}$ each independently represent a hydrogen atom, an alkyl group, an alkoxy group, or a halogen atom; and Ar represents an aryl group.

4. The method according to claim 3, wherein $R^{20}$ and $R^{<}$ in the general formula (4) each represent a hydrogen atom.

5. The method according to claim 3, wherein Ar in the general formula (4) is a phenyl group.

6. The method according to claim 3, wherein Ar in the general formula (4) is a tolyl group.

7. The method according to claim 1, further comprising adding phosphine as an additive to the reaction system.

8. The method according to claim 7, wherein the phosphine is trialkylphosphine, triarylphosphine, or alkyldiarylphosphine.

9. The method according to claim 1, wherein the allylating reagent represented by the general formula (2) is crothyltrichlorosilane.

10. The method according to claim 1, wherein the allylating reagent represented by the general formula (2) is 2-methyl-2-butenyltrichlorosilane.

11. The method according to claim 1, wherein the allylating reagent represented by the general formula (2) is allyltrichlorosilane.

12. A method for producing alloisoleusine, which uses as a key reaction, the asymmetric allylation reaction according to the method of claim 1.

* * * * *